US012712075B2

(12) United States Patent
Pinder et al.

(10) Patent No.: US 12,712,075 B2
(45) Date of Patent: Aug. 18, 2026

(54) COMMUNICATION SYSTEM, APPARATUS AND METHOD PROVIDING MASS CASUALTY INCIDENT REGISTRY SERVICE

(71) Applicant: MOTOROLA SOLUTIONS, INC., Chicago, IL (US)

(72) Inventors: Ellis A Pinder, Davie, FL (US); Hua Li, Plantation, FL (US); Devin Barreto, Davie, FL (US)

(73) Assignee: MOTOROLA SOLUTIONS, INC., Chicago, IL (US)

( * ) Notice: Subject to any disclaimer, the term of this patent is extended or adjusted under 35 U.S.C. 154(b) by 842 days.

(21) Appl. No.: 17/820,924

(22) Filed: Aug. 19, 2022

(65) Prior Publication Data

US 2024/0062893 A1 Feb. 22, 2024

(51) Int. Cl.

*G16H 40/67* (2018.01)
*G06F 16/955* (2019.01)
*G16H 10/60* (2018.01)
*G16H 40/20* (2018.01)

(52) U.S. Cl.

CPC ........... *G16H 40/67* (2018.01); *G06F 16/955* (2019.01); *G16H 10/60* (2018.01); *G16H 40/20* (2018.01)

(58) Field of Classification Search

CPC ........ G16H 40/67; G16H 10/60; G16H 40/20; G06F 16/955

See application file for complete search history.

(56) References Cited

U.S. PATENT DOCUMENTS

| | | | | |
|---|---|---|---|---|
| 7,999,741 | B2 | 8/2011 | Graves et al. | |
| 8,040,246 | B2 | 10/2011 | Graves et al. | |
| 8,054,177 | B2 | 11/2011 | Graves et al. | |
| 9,826,358 | B2 * | 11/2017 | Ryan | H04W 4/022 |
| 10,178,534 | B2 | 1/2019 | Barash et al. | |
| 11,522,972 | B1 * | 12/2022 | Hiraki | H04L 67/306 |

(Continued)

FOREIGN PATENT DOCUMENTS

| | | | | |
|---|---|---|---|---|
| CA | 2595830 A1 | | 2/2009 | |
| CN | 112397182 A | * | 2/2021 | G06F 16/29 |

OTHER PUBLICATIONS

Mei Li, et al. "System For Emergency Alarm And Receiving Alarm, Subsystem, Method And Storage Medium." PE2E English translated. (Year: 2021).*

(Continued)

*Primary Examiner* — Wesley L Kim
*Assistant Examiner* — Erkin Abdullaev
(74) *Attorney, Agent, or Firm* — Barbara R Doutre

(57) ABSTRACT

A system, method and apparatus provide a self-registration service to potential victims located in proximity to an incident event. An incident-specific URL is pushed to communication devices located in proximity to the incident. The incident-specific URL links to a self-registration website that enables victims to upload their health related information. The incident-specific URL and self-registration website enables identifying potential victims along with their health status for tracking during a mass casualty incident (MCI). The service may further include providing self-triage information and the tracking of "self-help" victims, with minor injuries. The service can further exchange information with health service providers (HSPs) to facilitate patient tracking and status updates.

11 Claims, 3 Drawing Sheets

(56) References Cited

U.S. PATENT DOCUMENTS

| | | | | |
|---|---|---|---|---|
| 12,273,799 | B2 * | 4/2025 | Martin | G06F 3/048 |
| 2004/0073453 | A1 * | 4/2004 | Nenov | G06Q 10/10 705/2 |
| 2008/0126417 | A1 * | 5/2008 | Mazurik | G06F 16/80 |
| 2011/0313783 | A1 | 12/2011 | Sacco et al. | |
| 2014/0019162 | A1 * | 1/2014 | Skowronski | G16H 40/20 705/3 |
| 2019/0159009 | A1 * | 5/2019 | Barash | H04M 1/72418 |
| 2019/0206520 | A1 * | 7/2019 | Eteminan | G16H 40/20 |
| 2019/0206549 | A1 | 7/2019 | Perry et al. | |
| 2020/0226551 | A1 * | 7/2020 | Saffari | H04L 67/306 |
| 2020/0258606 | A1 * | 8/2020 | Ferentz | G06F 16/245 |
| 2020/0329348 | A1 * | 10/2020 | Halun | H04W 4/08 |
| 2022/0037026 | A1 * | 2/2022 | Chang | G16H 20/00 |
| 2022/0115142 | A1 * | 4/2022 | Greenwood | G16H 40/63 |
| 2024/0015492 | A1 * | 1/2024 | Mckinley | G06Q 50/40 |

OTHER PUBLICATIONS

Eneim, Maryam, et al.: “Data Privacy Management Based on Conditional Thresholds”, U.S. Appl. No. 17/449,831, filed Oct. 4, 2021, all pages.

* cited by examiner

COMMUNICATION SYSTEM, APPARATUS AND METHOD PROVIDING MASS CASUALTY INCIDENT REGISTRY SERVICE

FIELD OF THE INVENTION

The present invention relates generally to communication systems and more particularly to communication systems aimed at collecting and tracking mass casualty incident information.

BACKGROUND

Communication systems, such as public safety communication systems, are relied upon during mass casualty incidents. The enormity and complexity of events taking place during a mass casualty incident presents challenges to public safety responders, health care workers, and individual family members seeking information. Acquiring and distributing victim information to appropriate recipients can be difficult because some victims may leave an incident scene if less severely injured, while others may be treated locally at the scene, and still others may be transported to one of several hospitals or treatment centers. Many victims may not be identified or tracked making any current incident response or post response follow-up very difficult. It is important that the most accurate and up-to-date victim information be tracked and shared in a timely manner so that public safety resources can be optimized for the current incident, as well for post event follow-up.

BRIEF DESCRIPTION OF THE FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
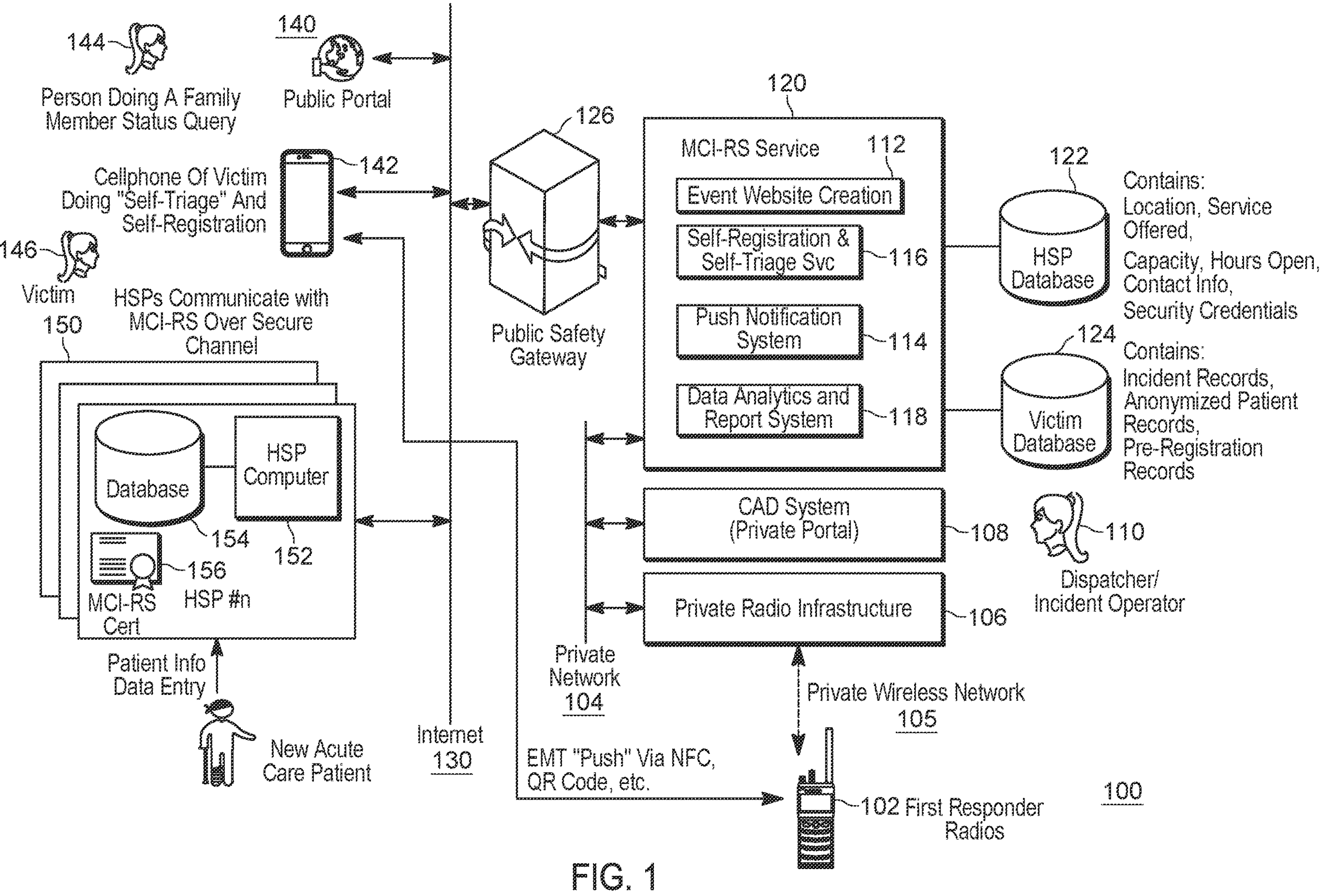
FIG. 1 is a communication system formed and operating in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

Briefly, there is provided a communication system, apparatus and method that provide a self-registration service that pushes/sends an incident-specific URL linked to a self-registration website to portable communication devices in vicinity of an incident. The self-registration website is created for each new incident and enables self registration of potential victims associated with the incident through their respective portable communication devices. The self-registration website includes questions/answers for the potential victim of the current incident. The responses are stored in a registry database. The registry database is also linked to public safety and medical casualty tracking systems. For the purposes of this application, a cell phone may also represent a personal tablet, a personal computer or other portable communication device operable over a public portal and having internet access. In some embodiments, a single self-registration website may be created that provides a self-registration webpage customized for each new incident.

When viewed from cell-phone end user perspective, the cell phone, having a microprocessor, transmitter, and receiver, receives a pushed incident-specific URL linked to a self-registration website associated with a current incident event occurring within a predetermined proximity of the portable communication device. The self-registration website includes queries associated with the self-registered user's health. The responses to those queries are transmitted from the cell phone to a registry database for tracking victim information. The self-registration website may further include self-triage information and triage queries to assess and provide recommendations for minor injuries, and direct the more seriously injured, self-registered users to a health care provider.

When viewed from an overall communication system perspective, the communication system includes a plurality of cell phone communication devices operating over public portal; a plurality of public safety communication devices, such as public safety radios, public safety tablets, public safety computers and the like, are communicatively coupled to a computer aided dispatch (CAD) system operating over a private network; a mass casualty incident response system (MCI-RS) integrated with the CAD system, the MCI-RS pushing new incident notifications including an incident-specific URL linked to a self-registration website to the plurality of cell phones; and a plurality of health service providers (HSPs) exchanging information with the MCI-RS over a secure internet connection.

The embodiments provide a method for managing a mass incident event, by: creating a new event instance, at a mass casualty incident response system, in response to receiving a new mass incident alert from a computer aided dispatch (CAD) system; notifying one or more health service providers (HSPs) of the newly created event instance; creating a self-registration website associated with the new event instance; pushing an event notification to communication devices within a predetermined proximity of the new mass incident, the event notification including a incident-specific URL linked to the self-registration website; receiving self-registration information from newly registered devices that self-registered with the public facing website; exchanging the self-registration information with the one or more HSPs; and generating periodic reports based on the exchanged information.

FIG. 1 shows a communication system 100 formed and operating in accordance with some embodiments. Communication system 100 comprises a plurality of public safety radios 102 operating over a private wireless network 105. The private wireless network 105 operates using private radio infrastructure 106, the private radio infrastructure 106 including at least one base station under the control of a controller. A private network 104 comprises at least one computer aided dispatch (CAD) system 108, operating as a private portal to a mass casualty incident response system (MCI-RS) 120, communicatively coupled with the system controller of the private radio infrastructure 106. The (CAD) system 108 is managed by a dispatch operator 110. The public safety radio 102 communicates with other like devices as well as with the CAD system 106 over private wireless network 105 and private network 104. The public safety radio 102 is operated by public safety personnel, such as fire rescue, law enforcements, EMT personnel and the like. While shown and described as public safety radio(s) 102, it is to be understood that other public safety communication devices, such as public safety tablets, public safety computers, and the like may be used.

In accordance with the embodiments, the communication system 100 further includes a mass casualty incident response system (MCI-RS) 120 that operates as a registry service. The MCI-RS 120 includes a plurality of sub-system modules including an event website creation module 112, a push notification module 114, self-registration and self-triage module 116, and data analytics and report module 118. In accordance with the embodiments, the CAD system 108 interoperates with the MCI-RS 120 to trigger creating an event instance for a current incident event reported to the CAD system, such as from a 911 call to the dispatcher 110, or received as an alert from the public safety radio 102. A health service provider (HSP) database 122 is operatively coupled to the MCI-RS 120. The HSP database 122 contains a list of HSPs and HSP operational parameters, such as location of HSP, service capabilities of HPS, patient capacity, hours of operation, contact information, and communication security credentials, to name a few. A victim database 124 is further operatively coupled to the MCI-RS 120, the patient database contains incident records, anonymized patient records, pre-registration records, and/or other patient related information. Victim database 124 may further include individuals who performed self-registration for an incident and subsequently elected not to seek any formal medical treatment.

The MCI-RS 120 is further communicatively coupled to a public safety gateway 126 to gain access over an internet connection 130 to a public portal 140. Operating within the public portal are personal communication devices, such as cell phone communication devices 142, which may be operated by their respective users, such as victim 146 or a family member 144. Again, for the purposes of this application, the cell phone 142 may also represent a personal tablet, a personal computer or other portable communication device operable over a public portal and having internet access.

The self-registration website may provide for data entry and/or voice entry type responses to the queries. In some embodiments, a single self-registration website may be created that refers to a self-registration webpage created and customized for each new incident. Data entry and/or voice responses may be entered via a user interface of the cell phone 142 (e.g. keypad, touch interface, pull down menus) and/or audio responses to website generated voice queries. Basic identity information (such as name, age, gender, injury type) of the potential victim is collected upon self-registration and transmitted through the public portal 140 and public safety gateway 126 to the victim database 124 associated with the MCI-RS 120. Pre-registration services may also be provided which collect and store limited personally identifiable information (PII), such as user name, emergency contact information, primary physician name, and critical medical information (e.g. drug allergies, medication with potentially severe interactions)—prior to any incident occurring. The self-registration website may further include self-triage queries and information for assessing types of injuries and/or concerns from the self-registered user. The MCI-RS 120 may communicate over the public portal 140 to route victims with minor injuries to HSPs, such as walk-in clinic, and attempt to avoid HSPs, such as major trauma hospitals, that are handling major injuries.

The MCI-RS 120 further communicates over the public safety gateway 126 via a secure communication path using internet 130 to a plurality of HSPs 150 (those HSPs having been listed in the HSP database 122) to obtain updates on current admission, capacity and available of services particular to the incident type. Current operational parameters can be compared to previously stored operational parameters associated with the one or more HSPs. The secure communication path, unique to each HSP, ensures private communications including patient information, patient loading/capacity, etc. between the HSPs 150 and the MCI-RS 120. Each HSP 150 includes its own respective HSP computer 152 and database 154, as well as security certification credential 156. Each HSP has its own communication security certification which aligns with the credentials stored in HSP database 122. The security credentials facilitate a secure communication path and HSP authentication between the HSP computer/database at 150 and the MCI-RS 120.

The secure communication path enables the MCI-RS 120 to query the status and loading from each HSP, query the need for MCI-RS incident tracking, and check availability/capacity of the public portal 140 to transfer incident related information between the MCI-RS 120 and HSPs 150.

Operationally, the MCI-RS 120 is notified by the CAD system 108 that an incident event is taking place. For example calls into 911 dispatch system or calls from the public safety radio 102 are processed through the CAD system 108 and a notification of the incident is received at the MCI-RS 120. The MCI-RS 120 creates a new incident event instance and notifies the HSPs 150 of the new incident event. The MCI-RS's event website creation module 112 then creates a public-facing website for self-registration associated with the event instance. The self-registration website may be configured for public and/or first responders.

The push notification module 114 then pushes an event notification; including an incident-specific uniform resource locator (URL), to cell phones within a predetermined distance of the incident event. The incident-specific URL provides a reference (an address) to a website having a webpage created for that particular incident. The URL may be a traditional URL and may include a query string. such as https://county.broward.org/incident?eventid=0x02455A68. Alternately, the URL can be a shortened URL such as that provided by www.tinyurl.com (TinyURL, LLC) or equivalent. Any technique to provide a URL or an IP address to a website (or webpage) may be used. For small-sized incidents the incident-specific URL may be communicated via PAN or LAN technology such as Wi-Fi, Bluetooth, or NFC. The communication may be initiated or managed by first responder radio 102 or by transportable computer intended for incident-scene management. The self-registration website may be configured for public citizens operating personal communication devices 142 and and/or first responders operating public safety radios. Information is then collected from the newly registered cell phone devices 142 and stored into victim database 124 for analytics, tracking, and subsequent report generation via data analytics and report module 118.

A new event notification is also pushed from push notification module 114, to HSPs 150, allowing preparation and triggering questions to determine if any new patient admissions to the HSP is associated with the event. For new patients that are determined to be associated with the incident, the HSP computer will cause a notification to be sent over the secure communication path over the internet 130 to the MCI-RS 120 identifying the patient and nature of the patient injury/treatment and/or association with the incident.

In accordance with the embodiments, mass incident alerts (input by dispatcher resulting from public 911 calls for first responder calls over private radio network 105) to the CAD system 108 trigger the MCI-RS 120 to begin creating an event, managing the event, and generating reports associated with the event. Information may be exchanged in both directions between the MCI-RS 20 and the HSPs 150 using a secure communication path of internet 130. The exchanged information may include current HSP operational parameters, patient information of registered victims; and general status information of patients not registered with the self-registration service. For example, incident information may be sent from the MCI-RS 120 to HSPs 150 along with inquiries pertaining to current staff availability, bed capacity, specialist availability, to name a few. The HSPs 150 can query the MCI-RS 120 to retrieve the registration information of the current registrants (registered victim information, registered interested party/family member). For example, a victim can perform registration using a phone or tablet at the event scene or during transport, and this information is conveyed to MCI-RS 120 into victim database 124, This information, including identify information, triage information and medical history, can then be retrieved by HSP 150 from MCI-RS 120 upon admission to HSP 150 thus saving time. HSP 150 can review, via HSP computer 152 and database 154, their respective patient lists, and notify the MCI-RS 120 of the presence of registered and unregistered victims at their facility.

Information can be sent from each HSP 150 providing a first high level status information, such as number of victims being treated and how many of those victims are registered. High level status updates may also include, notification from the HSPs 150 notifying the MCI-RS 120 of number of patients admitted to each HSP's emergency room, number of patients transferred to ICU, number of patients under stable condition, number transferred patients, number of discharged patients, allowing for well-tracked victims counts and their current location or status. Gender, age, and injury type may be included with the high-level notifications.

HSP information that includes private data pertaining to a self-registered victim may only be released from the HSPs 150 to the MCI-RS 120 in accordance with the terms and conditions of their respective self-registrations. For example, some registrants may limit certain facets of their private information to be released to the MCI-RS 120. Hence, a further more detailed level of status updates can be provided from the HSPs 150 to the MCI-RS 120 such as victim identity (if registration permitted access), pre-existing health conditions, long-term victim prognosis, follow-up therapy, medication prescriptions, and other private information pertaining to the self-registered victim.

The MCI-RS 120 may utilize data analytics included in the data analytics and report module 118 to generate periodic reports pertaining to victims associated with the incident. Some periodic reports may be utilized for intergovernmental purposes, such as sharing information between county run hospitals in proximity to the incident. The periodic reports can be provided across all the HSPs 150 participating in the incident and/or additional HSPs that may be needed to participate to help respond to a mass incident with many casualties.

Data analytics and report module 118 may further be used to ascertain status and location for individuals. This service may be available to approved parties, such as registered family members, to query the registry service to check on the status of a loved one. Periodic reports of high level information (number of victims admitted, number in ER, number in ICU, nature of injuries, age) for registered and non-registered victims facilitates high level load balancing at the HSPs 150, while the more detailed reports on registered victims and family members can be used for personal notifications, and responding to family tracking inquiries.

Figure 2:
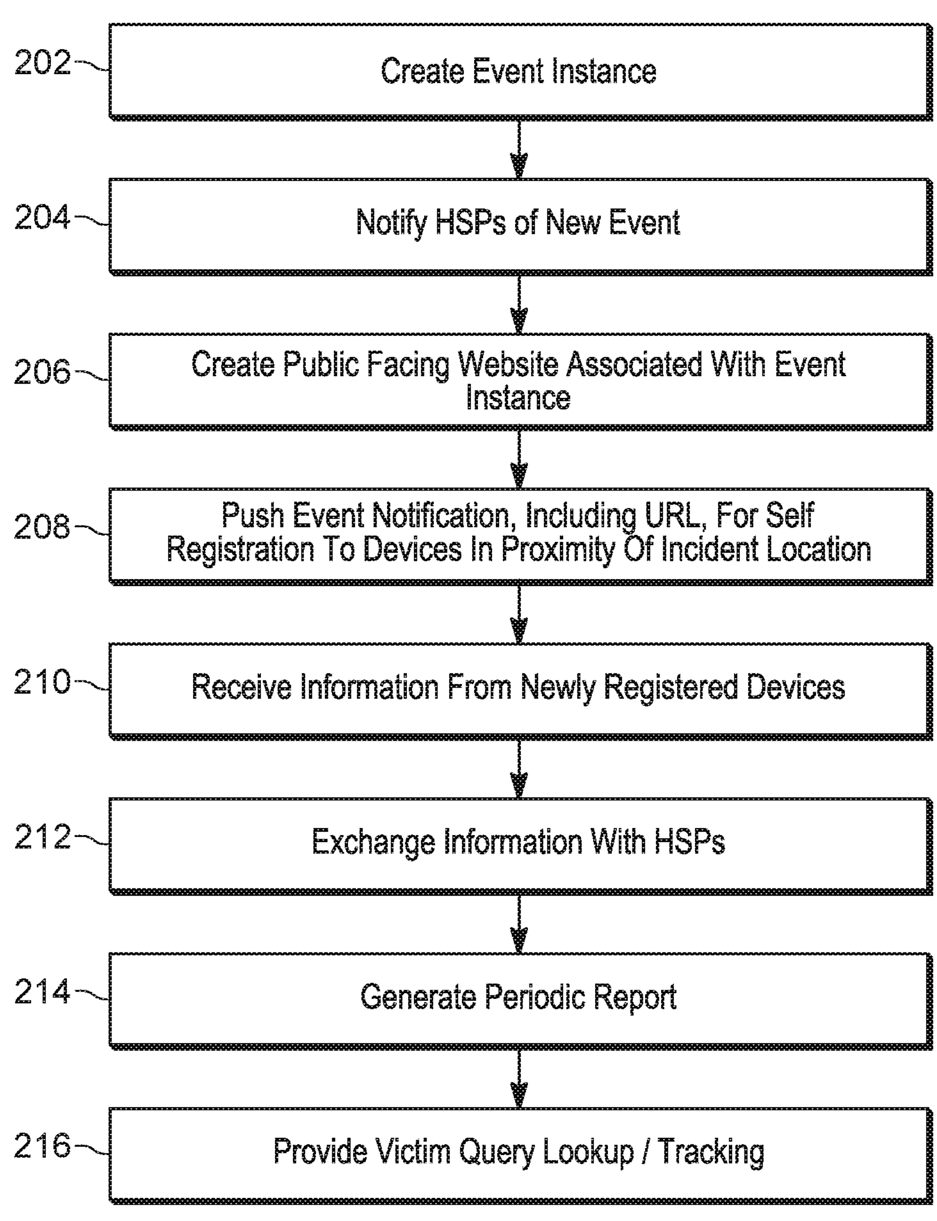
FIG. 2 is a flowchart of a method for managing a mass casualty incident in accordance with some embodiments.

FIG. 2 is a flowchart of a method for managing a mass casualty incident in accordance with some embodiments. The method 200 begins at 202 by creating an event instance. The event instance may be created at the MCI-RS 120 based on input received from a computer aided dispatch (CAD) system, such as the CAD system 108 of FIG. 1. The CAD system 108 may have been notified of the incident via a transmission from a first responder radio over the private wireless network 105 and private network 104 to the CAD system 106 and/or from a dispatcher input to the CAD system 108 in response to a 911 call. The MCI-RS then notifies a plurality of health service providers (HSPS) of the new event at 204. Event notifications to HSPs may be sent via a public safety gateway to set up a secure communication path over an internet connection as previously described.

The method continues at 206 with creating, at the MCI-RS, a public-facing website associated with the event instance. In accordance with the embodiments the public facing website includes at least a self-registration capability. The self-registration capability include queries specific to the type of incident event taking place. The public facing website may further include self-triage information to help assess and treat minor injuries of victims or others on the scene and/or generate "go to HSP" responses for assessments indicating more severe injuries.

In accordance with the embodiments, the MCI-RS-pushes the event notification, including a URL, for self-registration to devices in proximity of the incident location. For example, the push even notification may be pushed, over a cellular network, to cell phones operating within a predetermined location threshold of the incident. Such cell phones may belong to victims and/or other members of the public in proximity to the incident location. The website referenced by the pushed incident-specific URL may include triage information to help victims and members of the public assess and treat minor injuries and/or trigger a response that the individual should go to a HSP.

Additionally or alternatively, push event notifications may also be sent to first responder devices, such as public safety radios 102 of FIG. 1, over the private wireless network 105. The public safety radios 102 may then push the self-registration website to nearby cell phone communication devices, using short range communications, such as BLUETOOTH, near field communications (NFC) and the like. The self registration may include triage queries and information which can aid the final cell phone recipient in assessing and treating their own minor injuries or the minor injuries of others.

The MCI-RS receives the registration information including the responses to the self-triage queries at 210. This allows the MCI-RS to begin collecting and performing analytics on the received self-triage information The MCI-RS and HSPs start exchanging information at 212. For example, the MCI-RS can inform the HSPs as to how many victims have self-registered (with identity and without identity), the number of victims directed to seek assistance from an HSP, and the number of victims being treated for minor injuries via the self-triage information of the website. The HSP can communicate to the MCI-RS, the HSP capacity, admissions, injury types being treated, number of patients in ER, number of patients in ICU, and number of patients being transferred. The method continues at 214 by generating periodic reports, by the MCI-RS, based on the exchanged information with the HSPs and the received information from the cell phones. At 216, the method further enables providing look-up query and tracking of registered victims by other pre-approved registered users. For example, a cell phone user (or using personal computer or other personal communication) can pre-register their personal information with the MCI-RS providing permissions for certain individuals, such as family members, to seek out their status, should an incident occur into the future. Victims who self-register at the incident may also grant permission to the MCI-RS 120 to release status information to approved individuals per their registration.

Figure 3:
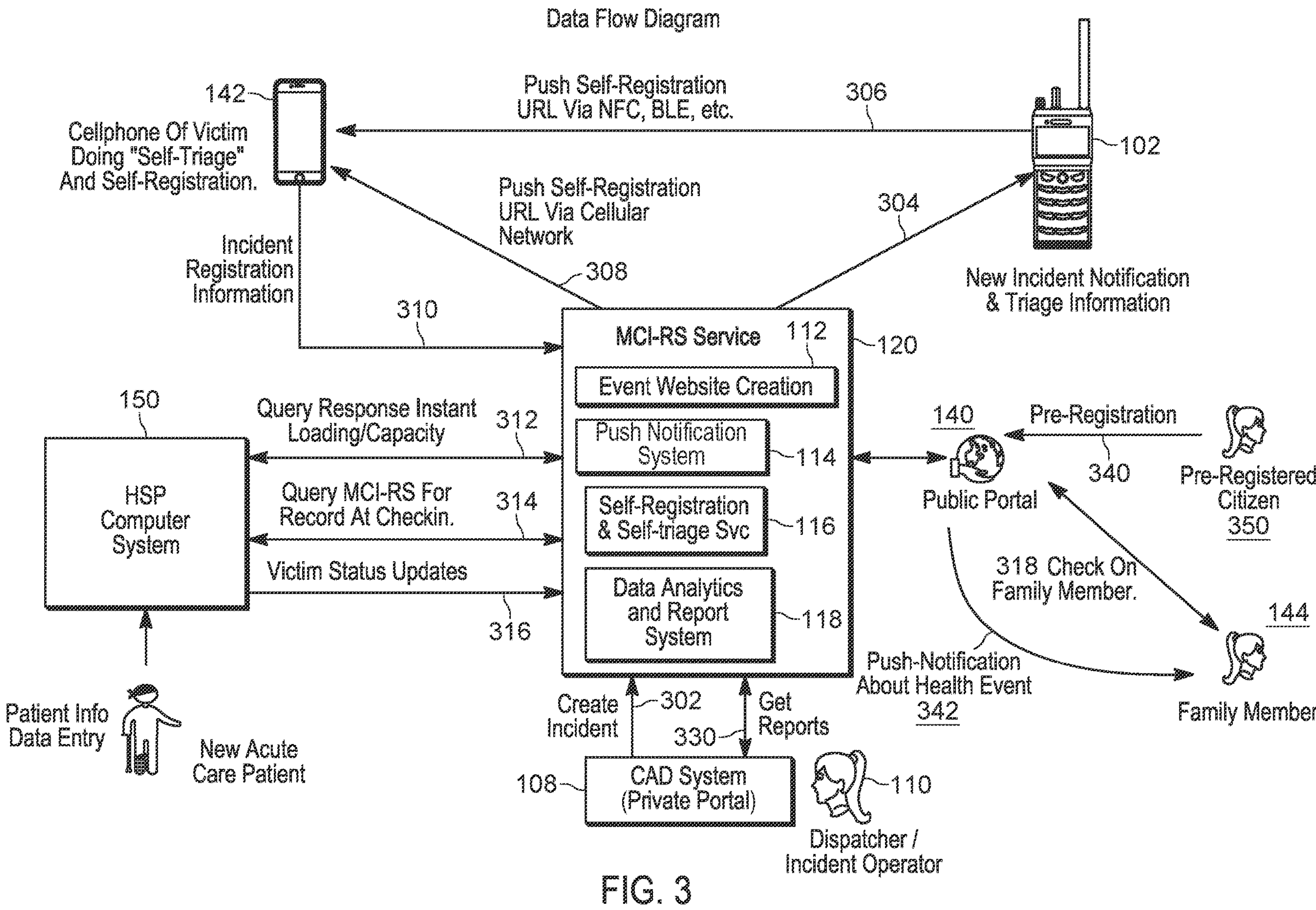
FIG. 3 is a use case example for managing a mass casualty incident using the system and method of FIGS. 1 and 2 in accordance with some embodiments.

FIG. 3 is a use case information flow example in accordance with some embodiments. Citizen 350 or a family member of Citizen 350 may pre-register with MCI-RS 120. Pre-registration is performed through a dedicated website operated by MCI-RS 120 through public portal 140. The pre-registration information includes identity information and emergency contact information, and may additionally include pertinent medial information useful in an emergency. If the MCI-RS 120 detects pre-registered citizen 350 becomes associated with an incident, then the push notification module 114 notifies at 342 emergency contacts, such as family member 144, via SMS, email, or other means. Pre-registered citizen 350 may become associated with an incident event through self-registration over the internet at 310 in response to an incident-specific URL/website pushed from the MCI-RS 120. Pre-registered citizen 350 may also become associated with an incident event via registration through incident-specific URL/website pushed from radio 102 (or other first-responder/EMT communication device). Pre-registered citizen 350 may also become associated with an incident event via admission to an HSP at 316. It is also possible that the first responders may enter registration and/or triage information on behalf of a victim through any internet connected device through the incident-specific URL/website.

Citizen 144 can access MCI-RS 120 through public portal 140 to ascertain the status of a family member. This operation may apply to either pre-registered citizen 350 or any victim 146 who is not pre-registered. Various security policies may be applied to control and/or limit access to this information. Citizen(s) 144 may have preregistered 340 with the MCI-RS 120 over the public portal.

In the event of a mass casualty incident, the CAD system 108 receives via dispatcher or 911 call-intake, a notification of the mass casualty incident and location. The CAD system notifies at 302 the MCI-RS 120 to create an event instance. This event instance is sent to one or more HSPs 150 and to radios 102. Subsequently, push notifications are sent at 304 to first responders, sent at 308 to victim cell phones, and sent at 342 to family members 144 of pre-registered citizens 350 that have been registered to the incident.

The MCRI-RS 120 notifies the HSPs 150 of the new incident and checks current HSP parameters, such as HSP current patient load, and patient capacity at 312. The current HSP operational parameters may be compared to pre-stored HSP operational parameters (database 122 of FIG. 1) to facilitate determining which HSPs are best suited to handle injuries associated with the incident.

The MCI-RS 120 uses its event website creation module 112 to create a public facing website associated with the event instance. The self-registration website provides a webpage that includes self-registration health queries and may further include triage assessment queries and triage self-help information generated from the self-registration and triage module 116. The website is accessible via an incident-specific URL created by the MCI-RS 120 and provided to devices within a predetermined proximity of the incident location.

The MCI-RS 120 pushes at 308 the incident-specific URL linking to the self-registration website over the internet to cell phones 142 within a predetermined proximity threshold of the incident location. Victim(s) associated with device(s) 142 respond with identity information and health responses over the internet at 310 as part of their self-registration which may further include responses to the self-triage queries.

Additionally or alternatively, the incident-specific URL linking to the self-registration website and triage information, may be sent at 304 over a private network to public safety radios 102 in proximity to, or dispatched to, the incident. The public safety radios 102 may then use short range communications (e.g. NFC, BLUETOOTH, PAN, or the like) to push 306 the self-registration and triage information to cell phones, tablets, and/or portable computers within a predetermined proximity of the incident location. Again, victim(s) associated with device(s) 142 may respond with identity information and health responses over the internet at 310 as part of their self-registration which may further include responses to the self-triage queries.

The MCI-RS 102 aims to provide the incident-specific URL linking to the self-registration website to as many potential victims as possible via the one more communication paths (i.e. MCI-RS-to-cell phone path and/or MCI-RS-to-radio-to-cell phone path).

The responses to the self-registration and self-triage queries are received by the MCI-RS 120 for processing via data analytics and report module 118. Updated reports may be sent to, or retrieved by, CAD system 108. The analytical results may be reported (e.g. periodically) at 330 via data analytics and report module 118 to a user interface, such as a print out or display, of CAD system 108. Additionally, data analytics and report module 118 will notify, via push notification system 114, about a health event 342 concerning preregistered citizens 350 that are associated with the event.

The MCI-RS 120 and the HSPs 150 exchange queries and responses updating each other's patient records upon HSP check-in. For example, if a patient performed the self-registration prior to HSP check-in, then the self-registration information will been sent from the MCI-RS 120 to the HSP 150. The HSP 150 is thus updated with the most current information pertaining to the patient. The self registration may include permissions for approved persons, such as family members 144, to retrieve 318, updated status reports pertaining to a particular patient at 318 via the public portal access to the MCI-RS 120. The MCI-RS 120 may also push updated and approved HSP patient information to approved emergency contacts, such as family members, in response to: a self-registered user being associated with the new incident; and the self-registered user entering or leaving an HSP associated with the new incident.

Accordingly, the various embodiments have provided for a system that deploys a self-registration service upon occurrence of an incident event. The self-registration service advantageously provides for a complete list of victims that can be identified and tracked during a mass casualty incident (MCI), including the tracking of "self-help" triage victims, with minor injuries. The system further beneficially enable first responders (FRs) to triage and transport more seriously injured victims while avoiding excessive overload on health service care providers. The system still further enables emergency contacts to locate and family members registered within the system and receive updates as to their medical status.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. A communication system, comprising:

a plurality of cell phone communication devices operating over a public internet portal;

a plurality of public safety radios communicatively coupled to a computer aided dispatch (CAD) system operating over a private network, wherein the plurality of public safety radios operate over a private wireless radio network under control of private radio infrastructure including at least one base station and a controller;

a mass casualty incident response system (MCI-RS) integrated with the CAD system, the MCI-RS pushing new incident notifications including an incident-specific URL linked to a self-registration website to the plurality of cell phone communication devices, wherein the self-registration website is configured to receive self-registration information from newly registered devices and store the self-registration information in a victim database associated with the MCI-RS; and a plurality of health service providers (HSPs) exchanging information with the MCI-RS over a secure internet connection, wherein the secure internet connection comprises a secure communication path unique to each HSP and based on HSP communication security credentials used for HSP authentication.

2. The communication system of claim 1, wherein the MCI-RS pushes the new incident notifications with incident-specific URL to the plurality of communication devices over one of:

a cellular network; and via short range communications from a public safety radio or public safety computer in proximity to the cell phone communication devices.

3. The communication system of claim 1, wherein the self-registration website includes health queries and a user interface for responding to the health queries via each cell phone communication devices of the plurality of cell phone communication devices.

4. The communication system of claim 3, wherein the self-registration website further includes self-triage information and self-triage queries.

5. The communication system of claim 4, wherein self-registration website health query responses and triage responses are retrieved by the MCI-RS and analyzed for periodic incident report generation.

6. The communication system of claim 5, wherein the periodic incident report generation is provided from the MCI-RS to the plurality of HSPs.

7. The communication system of claim 1, further comprising:

a first database for storing health service provider operational parameters pertaining to each of the plurality of HSPs; and a second database for storing patient information of pre-registered users and patient information of self-registered users associated with the new incident.

8. The communication system of claim 1, wherein the MCI-RS exchanges communications with the HSPs to determine:

current HSP operational parameters;

patient information of registered victims; and general status information of patients not registered with the self-registration website.

9. The communication system of claim 1, wherein the self-registration website collects personal identifiable information (PII) pertaining to self-registered users.

10. The communication system of claim 1, wherein the MCI-RS pushes the incident notification to emergency contacts in response to:

a self-registered user being associated with the new incident; and the self-registered user entering or leaving an HSP of the plurality of HSPs associated with the new incident.

11. The communication system of claim 1, wherein the self-registration website is part of an MCI response registry architecture that (i) is incident-instance specific and (ii) functions to collect newly registered device/user information and support exchange with HSPs.

* * * * *